(12) United States Patent
Lee et al.

(10) Patent No.: US 8,486,065 B2
(45) Date of Patent: Jul. 16, 2013

(54) RADIO-FREQUENCY ABLATION SYSTEM AND METHOD USING MULTIPLE ELECTRODES

(75) Inventors: Fred T. Lee, Madison, WI (US); Dieter Haemmerich, Madison, WI (US); John G. Webster, Madison, WI (US); Andrew S. Wright, Madison, WI (US); Chris D. Johnson, Madison, WI (US); David M. Mahvi, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1765 days.

(21) Appl. No.: 10/167,681

(22) Filed: Jun. 10, 2002

(65) Prior Publication Data
US 2002/0156472 A1 Oct. 24, 2002

Related U.S. Application Data

(63) Continuation-in-part of application No. 09/873,541, filed on Jun. 4, 2001, now abandoned.

(60) Provisional application No. 60/315,383, filed on Aug. 28, 2001, provisional application No. 60/210,103, filed on Jun. 7, 2000.

(51) Int. Cl.
*A61B 18/18* (2006.01)
(52) U.S. Cl.
USPC ............................................. 606/50; 606/34
(58) Field of Classification Search
USPC ........................................ 606/41–52, 32–34
See application file for complete search history.

(56) References Cited

U.S. PATENT DOCUMENTS

| | | | |
|---|---|---|---|
| 5,620,481 A * | 4/1997 | Desai et al. | 606/42 |
| 5,624,439 A | 4/1997 | Edwards et al. | |
| 5,634,921 A * | 6/1997 | Hood et al. | 606/5 |
| 5,672,174 A | 9/1997 | Gough et al. | |
| 5,683,384 A | 11/1997 | Gough et al. | |
| 5,728,143 A * | 3/1998 | Gough et al. | 606/42 |
| 5,735,847 A | 4/1998 | Gough et al. | |
| 5,800,484 A | 9/1998 | Gough et al. | |
| 5,836,906 A | 11/1998 | Edwards | |
| 5,902,272 A | 5/1999 | Eggers et al. | |

(Continued)

FOREIGN PATENT DOCUMENTS

WO WO 00/06046 2/2000

OTHER PUBLICATIONS

Eung Je Woo, et al., A New Catheter Design Using Needle Electrode for Subendocardial RF Ablation of Ventricular Muscles: Finite Element Analysis and in vitro Experiments, IEEE Transactions on Biomedical Engineering, vol. 47, No. 1, Jan. 2000.

Supan Tungjitkusolmun et al., Finite Element Analyses of Unfirom Current Density Electrodes for Radio-Frequency Cardiac Ablation, IEEE Transactions on Biomedical Engineering, vol. 47, No. 1, Jan. 2000.

*Primary Examiner* — David Shay
(74) *Attorney, Agent, or Firm* — Boyle Fredrickson S.C.

(57) ABSTRACT

Efficient ablation with multiple electrodes is obtained by rapidly switching electric power to the electrodes. In this way, shielding effects caused by the field around each electrode which would otherwise create cool spots, are avoided. Complex inter-electrode current flows are also avoided.

14 Claims, 4 Drawing Sheets

U.S. PATENT DOCUMENTS

| | | |
|---|---|---|
| 5,928,229 A | 7/1999 | Gough et al. |
| 5,951,547 A | 9/1999 | Gough et al. |
| 5,968,041 A * | 10/1999 | Edwards .................. 606/41 |
| 6,066,139 A | 5/2000 | Ryan et al. |
| 6,071,280 A | 6/2000 | Edwards et al. |
| 6,080,150 A * | 6/2000 | Gough ..................... 606/41 |
| 6,254,598 B1 | 7/2001 | Edwards et al. |
| 6,461,351 B1 * | 10/2002 | Woodruff et al. ......... 606/32 |

* cited by examiner

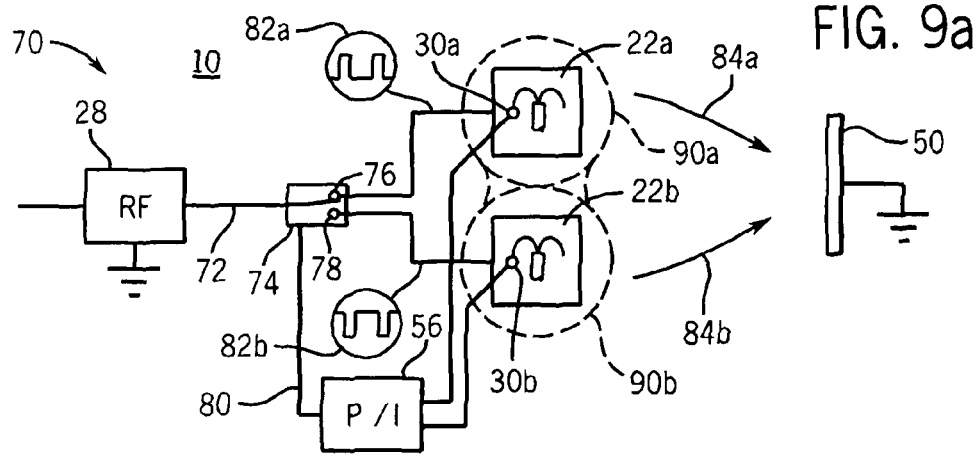
FIG. 9a
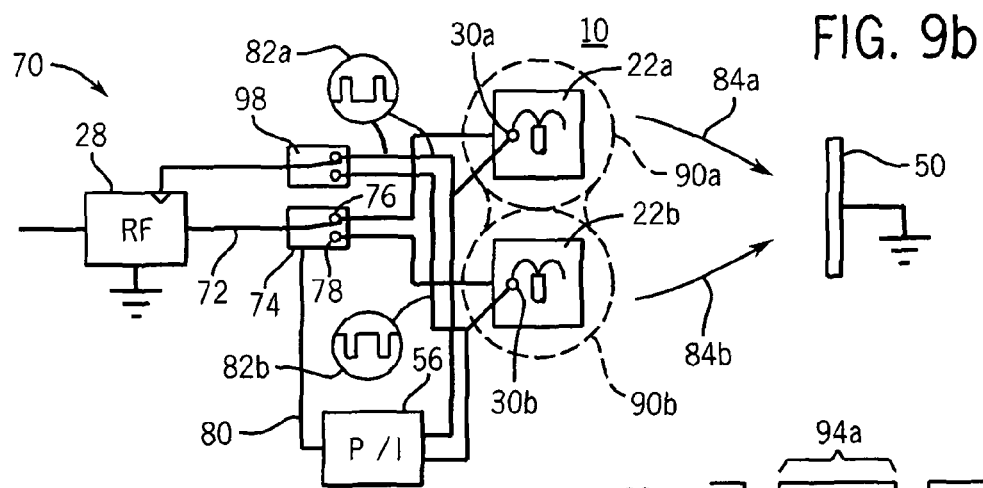
FIG. 9b
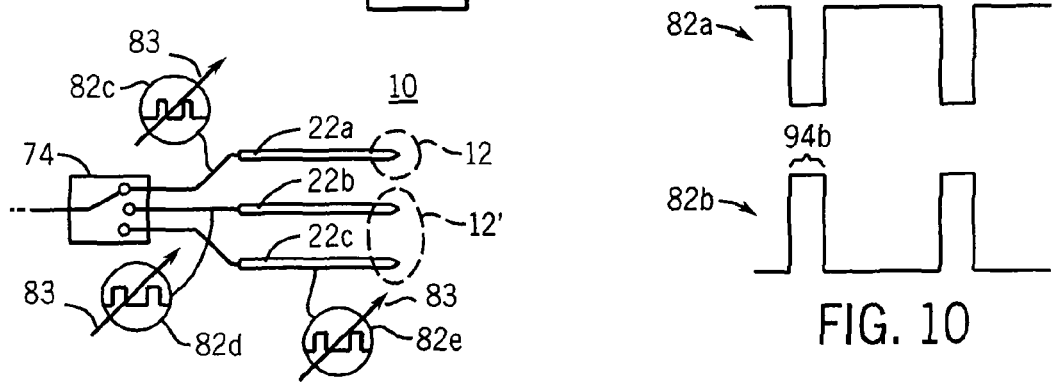
FIG. 10
FIG. 11
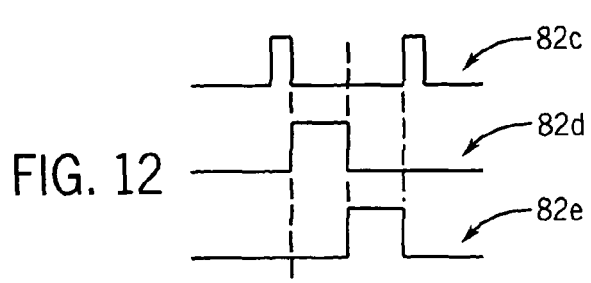
FIG. 12

RADIO-FREQUENCY ABLATION SYSTEM AND METHOD USING MULTIPLE ELECTRODES

CROSS-REFERENCE TO RELATED APPLICATIONS

This application claims the benefit of provisional application Ser. No. 60/315,383 filed Aug. 28, 2001, entitled "A Device to Allow Simultaneous Multiple Probe Use During Application of Radio Therapy"; hereby incorporated by reference, and is further a continuation-in-part of U.S. application Ser. No. 09/873,541 filed Jun. 4, 2001 now abandoned claiming the benefit of provisional application Ser. No. 60/210,103 filed Jun. 7, 2000 entitled "Multipolar Electrode System for Radio-frequency Ablation".

STATEMENT REGARDING FEDERALLY SPONSORED RESEARCH OR DEVELOPMENT

This application was made with United States government support awarded the following agency: NIH HL56143. The United States has certain rights in this invention.

BACKGROUND OF THE INVENTION

The present invention relates to radio-frequency ablation of tumors and the like and, in particular, to a device allowing for the simultaneous use of multiple ablation electrodes.

Ablation of tumors, such as liver (hepatic) tumors, uses heat or cold to kill tumor cells. In cryosurgical ablation, a probe is inserted during an open laparotomy and the tumor is frozen. In radio-frequency ablation (RFA), an electrode is inserted into the tumor and current passing from the electrode into the patient (to an electrical return typically being a large area plate on the patient's skin) destroys the tumor cells through resistive heating.

A simple RFA electrode is a conductive needle having an uninsulated tip placed within the tumor. The needle is energized with respect to a large area contact plate on the patient's skin by an oscillating electrical signal of approximately 460 kHz. Current flowing radially from the tip of the needle produces a spherical or ellipsoidal zone of heating (depending on the length of the exposed needle tip) and ultimately a lesion within a portion of the zone having sufficient temperature to kill the tumor cells. The size of the lesion is limited by fall-off in current density away from the electrode (causing reduced resistive heating), loss of heat to the surrounding tissue, and limits on the amount of energy transferred to the tissue from the electrode. The electrode energy is limited to avoid charring, boiling and vaporization of the tissue next to the electrode, a condition that greatly increases the resistance between the electrode and the remainder of the tumor. The tissue next to the electrode chars first because of the high current densities close to the electrode and thus creates a bottleneck in energy transfer.

Several approaches have been developed to increase energy delivered to tissue without causing charring. A first method places temperature sensors in the tip of the electrode to allow more accurate monitoring of temperatures near the electrode and thereby to allow a closer approach to those energies just short of charring. A second method actively cools the tip of the electrode with circulated coolant fluids within the electrode itself. A third method increases the area of the electrode using an umbrella-style electrode in which three or more electrode wires extend radially from the tip of the electrode shaft after it has been positioned in the tumor. The greater surface area of the electrode reduces maximum current densities. A fourth method injects a liquid (usually saline) into the tissue to increase conductivity. The effect of all of these methods is to increase the amount of energy deposited into the tumor and thus to increase the lesion size allowing more reliable ablation of more extensive tumors.

A major advantage of RFA in comparison to cryosurgical ablation is that it may be delivered percutaneously, without an incision, and thus with less trauma to the patient. In some cases, RFA is the only treatment the patient can withstand. Further, RFA can be completed while the patient is undergoing a CAT scan.

Nevertheless, despite the improvements described above, RFA often fails to kill all of the tumor cells and, as a result, tumor recurrence rates of as high as 50% have been reported.

The parent application to the present application describes a system of increasing the effective lesion size through the use of a bipolar operating mode where current flows between two locally placed umbrella electrodes rather than between an individual electrode and a large area contact plate. The bipolar current flow "focuses" the energy on the tumor volume between the two umbrella electrodes producing a lesion greater in volume with higher heating and more current density between electrodes than would be obtained by a comparable number of monopolar umbrella electrodes operating individually. In this respect, the bipolar operation allows treatment of larger tumors and more effective treatment of targeted tumors due to greater tissue heating with a single placement of electrodes, improving the speed and effectiveness of the procedure and making it easier to determine the treated volume over procedures where an individual electrode is moved multiple times.

The bipolar technique has some disadvantages. First, it is sensitive to the relative orientation of the two probes. Portions of the probes that are closer to each other will get hotter. Another disadvantage is that for two probe, bipolar systems, all the current exiting the first probe must enter the second probe depositing equal energy near both probes. This can be a problem when one probe is at a location, for example, near a cooling blood vessel, that requires additional deposition energy or independent control of that probe. Generally, too, a single set of bipolar probes can't treat multiple separated tumors.

One alternative is the simultaneous use of multiple probes in monopolar configuration. Here, as with the bipolar technique, the probes may be inserted at one time improving the speed of the procedure and eliminating ambiguity in the treatment volume that may come from repositioning probes. Current flows from each probe to the contact plate on the surface of the patient's skin.

A drawback to this multiple monopolar mode is that the monopolar probes may electrically shield each other causing insufficient heating between the probes. To the extent that the probes are operated at different voltages to accommodate local cooling of one probe, complex current flows can be created both between probes, and between probes and the contact plate making prediction of the ultimate effect of the probes difficult.

BRIEF SUMMARY OF THE INVENTION

The present inventors have developed a technique that combines the benefits of the bipolar probe operation in promoting large and uniform lesion sizes and the benefits of multiple, monopolar probe operation in providing individual control of the heating in the vicinity of each probe. The technique uses multiple monopolar probes operated in interleaved fashion, with a circuit switching rapidly between individual probes so that on an instantaneous basis, each probe is operating in isolation. Yet, for the purpose of heating, each probe can be considered to be operating simultaneously. Electrical shielding is reduced between probes while treatment speed is increased, the treated volume is more certain, and individual temperature, impedance, and/or time control of the probes is obtained.

Specifically then, the present invention provides a radio-frequency ablation system having at least three electrodes (possibly including a grounding pad) positionable in contact with a patient. A radio-frequency power source is connected through a switch system with the electrodes to sequentially connect at least one pair of the electrodes to the power source to provide for ablative current flow between the connected electrodes while inhibiting current flow between at least one unconnected pair. In the case of three electrodes, one electrode may be a surface contact, "grounding" electrode of broad area, and the other two internal electrodes positioned in or near the tumor volume. The switch system may operate to connect one of the percutaneous electrodes and the skin contact electrode together across the power supply and then the other of the percutaneous electrodes and the skin contact electrode together across the power supply. The switch system may be realized in electronic, electromechanical or other fashion.

Thus, it is one object of the invention to provide simultaneous multiple probe treatment of the tumor volume with more uniform lesion size by eliminating shielding effects caused by simultaneous operation of two adjacent probes.

The two probes may be umbrella electrodes having at least electrode wires extending from a common shaft.

Thus, it is another object of the invention to provide for larger lesions promoted by umbrella-type probes. The two electrodes may also be needle electrodes, with or without internal cooling.

The electronic switch may control the relative duration of connection of the pairs of electrodes to the power supply according to a controlled parameter of impedance, temperature, power, absolute time, or the difference between the impedance, temperature, or power of one or more electrodes.

Thus, it is another object of the invention to provide a simple means of independently controlling the power delivered to each of the electrodes using the switching means, which also provides for sequencing through the independent electrodes.

The electronic switch may include a proportional/integrator other controller controlling the switch according to the parameter of impedance, time, electrode power, or electrode temperature.

Thus it is another object of the invention to provide a simple method of adding more sophisticated control to the operation of the electrodes than may be provided simply through the RF power supply itself.

The switch system may control the voltage, or current or power that is applied to each electrode independently for the duration of application of electricity to each electrode.

Thus, it is another object of the invention to control the applied power, current or voltage, independently, according to the parameter of impedance, electrode power, or electrode temperature or the like.

The invention provides for a method in which there may be placed at least three electrodes in simultaneous contact with a patient where the electrodes may be sequentially connected to a radio-frequency power source to provide ablative current flow between a connected pair of the electrodes while inhibiting current flow between an unconnected pair.

Thus it is another object of the invention to allow a single step of insertion of multiple electrodes to speed treatment while obtaining the benefits in lesion control that are provided by moving a single electrode about in the patient. It is another object of the invention to eliminate ambiguities in treatment by a simultaneous insertion of the necessary electrodes before treatment.

The foregoing and other objects and advantages of the invention will appear from the following description. In this description, reference is made to the accompanying drawings, which form a part hereof, and in which there is shown by way of illustration, a preferred embodiment of the invention. Such embodiment and its particular objects and advantages do not define the scope of the invention, however, and reference must be made therefore to the claims for interpreting the scope of the invention.

BRIEF DESCRIPTION OF THE DRAWINGS

FIG. 9a is a schematic block diagram of a second embodiment of the invention providing for multiplexed monopolar operation of multiple electrodes and showing a controller connecting a radio-frequency source to multiple, monopolar electrodes through a switch cycling between the electrodes and FIG. 9b is a variation of the embodiment of FIG. 9a;

FIG. 10 is a timing diagram of the operation of the switch of FIGS. 9a and 9b showing complimentary operation of two electrodes and control of the duty-cycle of operation for further electrode control;

FIG. 11 is a fragmentary view of a further embodiment of the switch of FIGS. 9a and 9b showing its extension for operation of three electrodes; and FIG. 12 is a timing diagram of the power received by the electrodes using a switch per the embodiment of FIG. 11.

DETAILED DESCRIPTION OF THE PREFERRED EMBODIMENT

I. Bipolar Electrode Operation

Figure 1:
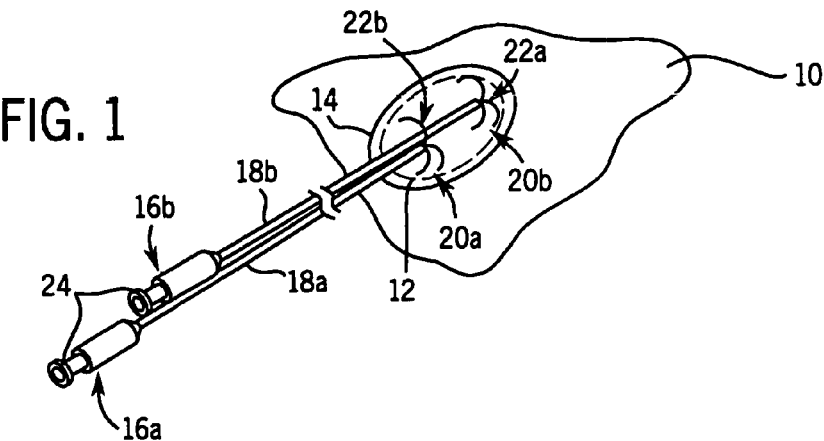
FIG. 1 is a perspective view of two umbrella electrode assemblies providing first and second electrode wires deployed per an allied embodiment of the present invention at opposite edges of a tumor to create a lesion encompassing the tumor by a passing current between the electrodes.

Referring now to FIG. 1, a liver 10 may include a tumor 12 about which a lesion 14 will be created by the present invention using two umbrella-type electrode assemblies 16a and 16b having a slight modification as will be disclosed below. Each electrode assembly 16a and 16b has a thin tubular metallic shaft 18a and 18b sized to be inserted percutaneously into the liver 10. The shafts 18a and 18b terminate, respectively, at shaft tips 20a and 20b from which project trifurcated electrodes 22a and 22b are formed of wires 32. The wires 32 are extended by means of a plunger 24 remaining outside the body once the shafts 18a and 18b are properly located within the liver 10 and when extended, project by an extension radius separated by substantially equal angles around the shaft tips 20a and 20b. The exposed ends of the wires 32 are preformed into arcuate form so that when they are extended from the shafts 18a and 18b they naturally splay outward in a radial fashion. Although the shafts 18a and 18b are shown axially parallel, this is not required and other orientations may be used.

Umbrella electrode assemblies 16a and 16b of this type are well known in the art, but may be modified in one embodiment of the invention, by providing electrical insulation to all outer surfaces of the shafts 18a and 18b and by insulating the tips of the exposed portions of the wires 32. This is in contrast to prior art, umbrella electrode assemblies, which leave the shaft tips 20a and 20b uninsulated and which do not insulate the wires 32. The purpose and effect of these modifications will be described further below.

Per the present invention, the first electrode 22a is positioned at one edge of the tumor 12 and the other electrode 22b positioned opposite the first electrode 22a across the tumor 12 center. The term "edge" as used herein refers generally to locations near the periphery of the tumor 12 and is not intended to be limited to positions either in or out of the tumor 12, whose boundaries in practice may be irregular and not well known. Of significance to the invention is that a part of the tumor 12 is contained between the electrodes 22a and 22b.

Figure 2:
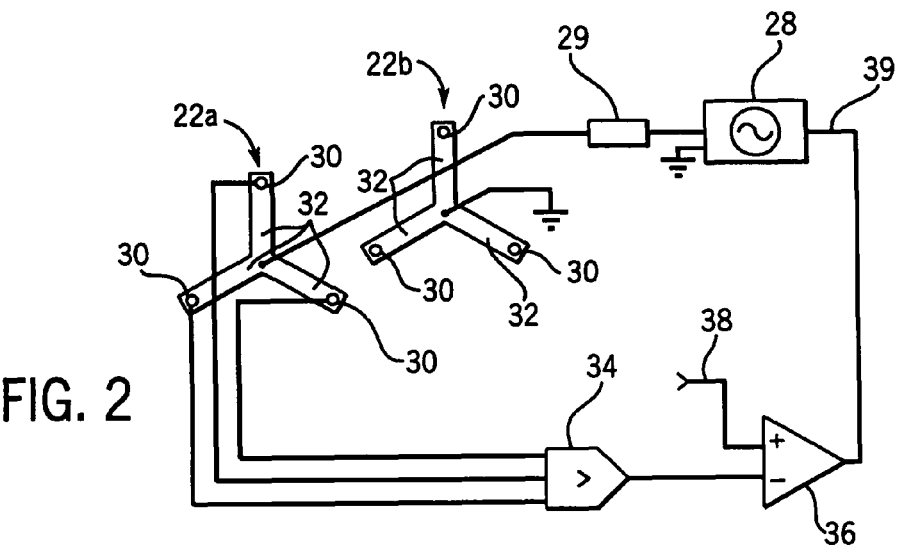
FIG. 2 is a schematic representation of the electrodes of FIG. 1 as connected to a voltage-controlled oscillator and showing temperature sensors on the electrode wires for feedback control of oscillator voltage.

Referring now to FIGS. 1 and 2, electrode 22a may be attached to a voltage-controlled power oscillator 28 of a type well known in the art providing a settable frequency of alternating current power whose voltage amplitude (or current or power output) is controlled by an external signal. The return of the power oscillator 28 is connected to electrodes 22b also designated as a ground reference. When energized, the power oscillator 28 induces a voltage between electrodes 22a and 22b causing current flow therebetween.

Figure 4:
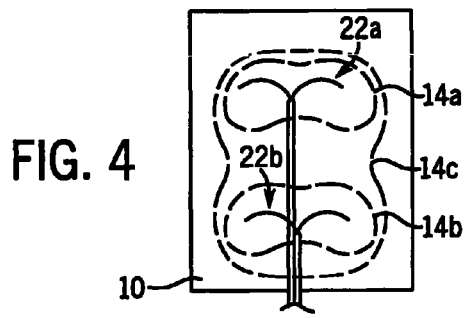
FIG. 4 is a simplified elevational cross-section of a tumor showing the first and second electrode positions and comparing the lesion volume obtained from two electrodes operating per the present invention, compared to the lesion volume obtained from two electrodes operating in a monopolar fashion.

Referring now to FIG. 4, prior art operation of each electrode 22a and 22b being referenced to a skin contract plate (not shown) would be expected to produce lesions 14a and 14b, respectively, per the prior art. By connecting the electrodes as shown in FIG. 2, however, with current flow therebetween, a substantially larger lesion 14c is created. Lesion 14c also has improved symmetry along the axis of separation of the electrodes 22a and 22b. Generally, it has been found preferable that the electrodes 22a and 22b are separated by 2.5 to 3 cm for typical umbrella electrodes or by less than four times their extension radius.

Referring again to FIG. 2, temperature sensors 30, such as thermocouples, resistive or solid-state-type detectors, may be positioned at the distal ends of each of the exposed wires 32 of the tripartite electrodes 22a and 22b. For this purpose, the wires 32 may be small tubes holding small conductors and the temperature sensors 30 as described above. Commercially available umbrella-type electrode assemblies 16a and 16b currently include such sensors and wires connecting each sensor to a connector (not shown) in the plunger 24.

In a first embodiment, the temperature sensors 30 in electrode 22a are connected to a maximum determining circuit 34 selecting for output that signal, of the three temperature sensors 30 of electrode 22 that has the maximum value. The maximum determining circuit 34 may be discrete circuitry, such as may provide precision rectifiers joined to pass only the largest signal, or may be implemented in software by first converting the signals from the temperature sensors 30 to digital values, and determining the maximum by means of an executed program on a microcontroller or the like.

The maximum value of temperature from the temperature sensors 30 is passed by a comparator 36 (which also may be implemented in discrete circuitry or in software), which compares the maximum temperature to a predetermined desired temperature signal 38 such as may come from a potentiometer or the like. The desired temperature signal is typically set just below the point at which tissue boiling, vaporization, or charring will occur.

The output from the comparator 36 may be amplified and filtered according to well known control techniques to provide an amplitude input 39 to the power oscillator 28. Thus, it will be understood that the current between 22a and 22b will be limited to a point where the temperature at any one of temperature sensors 30 approaches the predetermined desired temperature signal 38.

While the power oscillator 28 as described provides voltage amplitude control, it will be understood that current amplitude control may instead also be used. Accordingly, henceforth the terms voltage and current control as used herein should be considered interchangeable, being related by the impedance of the tissue between the electrodes 22b and 22a.

In an alternative embodiment, current flowing between the electrodes 22a and 22b, measured as it flows from the power oscillator 28 through a current sensor 29, may be used as part of the feedback loop to limit current from the power oscillator 28 with or without the temperature control described above.

In yet a further embodiment, not shown, the temperature sensors 30 of electrode 22b may also be provided to the maximum determining circuit 34 for more complete temperature monitoring. Other control methodologies may also be adopted including those provided for weighted averages of temperature readings or those anticipating temperature readings based on their trends according to techniques known to those of ordinary skill in the art.

Figure 3:
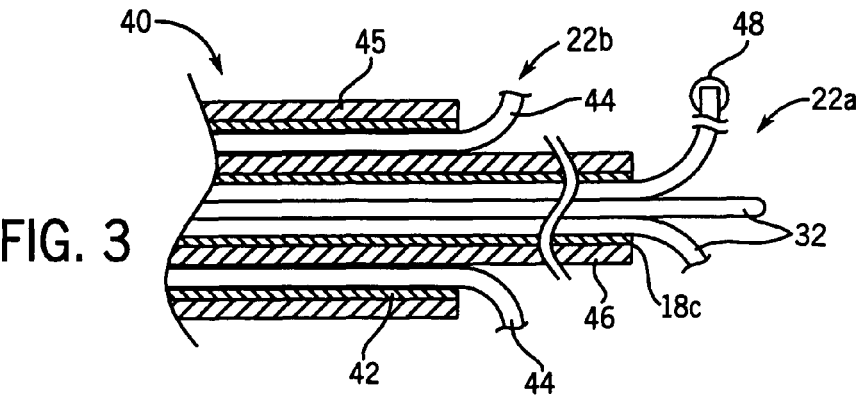
FIG. 3 is a fragmentary cross-sectional view of a tip of a combined electrode assembly providing for the first and second electrode wires of FIG. 1 extending from a unitary shaft arranging the wires of the first and second electrodes in concentric tubes and showing an insulation of the entire outer surface of the tubes and of the tips of the electrode wires.

Referring now to FIG. 3, the difficulty of positioning two separate electrode assemblies 16a and 16b per FIG. 1 may be reduced through the use of a unitary electrode 40 having a center tubular shaft 18c holding within its lumen, the wires 32 of first electrode 22a and a second concentric tubular shaft 42 positioned about shaft 18c and holding between its walls and shaft 18c wires 44 of the second electrode 22b. Wires 44 may be tempered and formed into a shape similar to that of wires 32 described above. Shafts 18c and 42 are typically metallic and thus are coated with insulating coatings 45 and 46, respectively, to ensure that any current flow is between the exposed wires 32 rather than the shafts 18c and 42.

As mentioned above, this insulating coating 46 is also applied to the tips of the shafts 18a and 18b of the electrode assemblies 16a and 16b of FIG. 1 to likewise ensure that current does not concentrate in a short circuit between the shafts 18a and 18b but, in fact, flows from the wires 32 of the wires of electrodes 22a and 22b.

Other similar shaft configurations for a unitary electrode 40 may be obtained including those having side-by-side shafts 18a and 18b attached by welding or the like.

Kits of unitary electrode 40 each having different separations between first electrode 22a and second electrode 22a may be offered suitable for different tumor sizes and different tissue types.

As mentioned briefly above, in either of the embodiments of FIGS. 1 and 3, the wires 32 may include insulating coating 46 on their distal ends removed from shafts 18c and 42 to reduce high current densities associated with the ends of the wires 32.

In a preferred embodiment, the wires of the first and second electrodes 22a and 22b are angularly staggered (unlike as shown in FIG. 2) so that an axial view of the electrode assembly reveals equally spaced non-overlapping wires 32. Such a configuration is also desired in the embodiment of FIG. 2, although harder to maintain with two electrode assemblies 16a and 16b.

Figure 6:
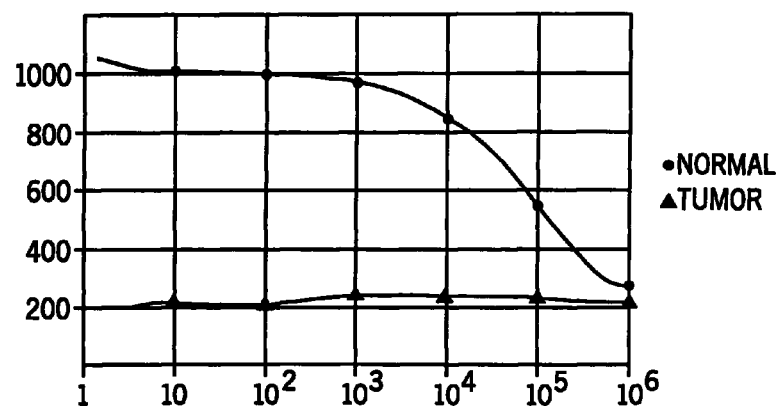
FIG. 6 is a graph plotting resistivity in ohm-centimeters vs. frequency in hertz for tumorous and normal liver tissue, showing their separation in resistivity for frequencies below approximately 100 kHz.

The frequency of the power oscillator 28 may be preferentially set to a value much below the 450 kHz value used in the prior art. Referring to FIG. 6, at less than 100 kHz and being most pronounced and frequencies below 10 kHz, the impedance of normal tissue increases to significantly greater than the impedance of tumor tissue. This difference in impedance is believed to be the result of differences in interstitial material between tumor and regular cell tissues although the present inventors do not wish to be bound by a particular theory. In any case, it is currently believed that the lower impedance of the tumorous tissue may be exploited to preferentially deposit energy in that tissue by setting the frequency of the power oscillator 28 at values near 10 kHz. Nevertheless, this frequency setting is not required in all embodiments of the present invention.

Importantly, although such frequencies may excite nerve tissue, such as the heart, such excitation is limited by the present bipolar design.

Figure 5:
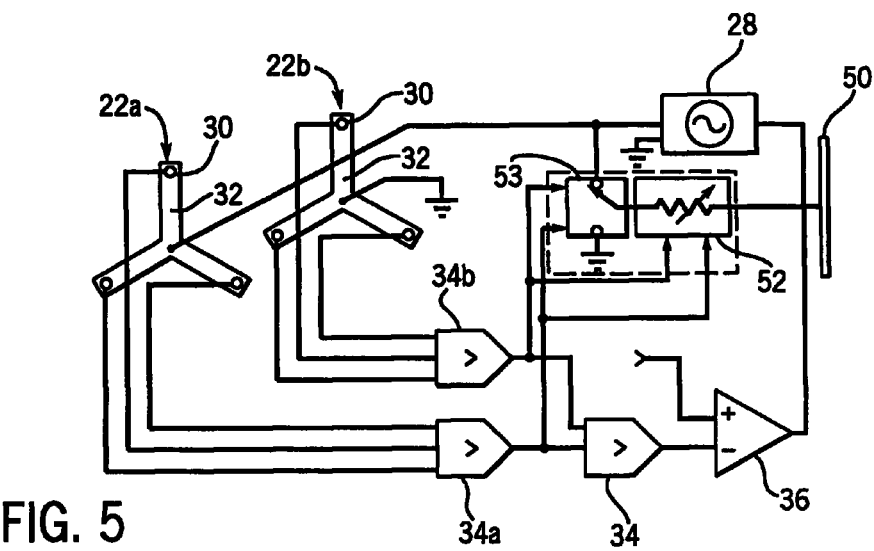
FIG. 5 is a figure similar to that of FIG. 2 showing electrical connection of the electrodes of FIG. 1 or FIG. 3 to effect a more complex control strategy employing temperature sensing from each of the first and second electrodes and showing the use of a third skin contact plate held in voltage between the two electrodes so as to provide independent current control for each of the two electrodes.

Referring now to FIG. 5, the local environment of the electrodes 22a and 22b may differ by the presence of a blood vessel or the like in the vicinity of one electrode such as substantially reduces the heating of the lesion 14 in that area. Accordingly, it may be desired to increase the current density around one electrode 22a and 22b without changing the current density around the other electrode 22a and 22b. This may be accomplished by use of a skin contact plate 50 of a type used in the prior art yet employed in a different manner in the present invention. As used herein, the term contact plate 50 may refer generally to any large area conductor intended but not necessarily limited to contact over a broad area at the patient's skin.

In the embodiment of FIG. 5, the contact plate 50 may be referenced through a variable resistance 52 to either the output of power oscillator 28 or ground per switch 53 depending on the temperature of the electrodes 22a and 22b. Generally, switch 53 will connect the free end of variable resistance 52 to the output of the power oscillator 28 when the temperature sensors 30 indicate a higher temperature on electrode 22b than electrode 22a. Conversely, switch 53 will connect the free end of variable resistance 52 to ground when the temperature sensors 30 indicate a lower temperature on electrode 22b than electrode 22a. The comparison of the temperatures of the electrodes 22a and 22b may be done via maximum determining circuits 34a and 34b, similar to that described above with respect to FIG. 2. The switch 53 may be a comparator-driven, solid-state switch of a type well known in the art.

The output of the maximum-determining circuits 34a and 34b each connected respectively to the temperature sensors 30 of electrodes 22a and 22b may also be used to control the setting of the variable resistance 52. When the switch 53 connects the resistance 52 to the output of the power oscillator 28, the maximum-determining circuits 34a and 34b serve to reduce the resistance of resistance 52 as electrode 22b gets relatively hotter. Conversely, when the switch 53 connects the resistance 52 to ground, the maximum-determining circuits 34a and 34b serve to reduce the resistance of resistance 52 as electrode 22a gets relatively hotter. The action of the switch 53 and variable resistance 52 is thus generally to try to equalize the temperature of the electrodes 22a and 22b.

If electrode 22a is close to a heat sink such as a blood vessel when electrode 22b is not, the temperature sensors 30 of electrode 22a will register a smaller value and thus, the output of maximum-determining circuit 34a will be lower than the output of maximum-determining circuit 34b.

The resistance 52 may be implemented as a solid-state device according to techniques known in the art where the relative values of the outputs of maximum-determining circuits 34a and 34b control the bias and hence resistance of a solid-state device or a duty-cycle modulation of a switching element or a current controlled voltage source providing the equalization described above.

Figure 7:
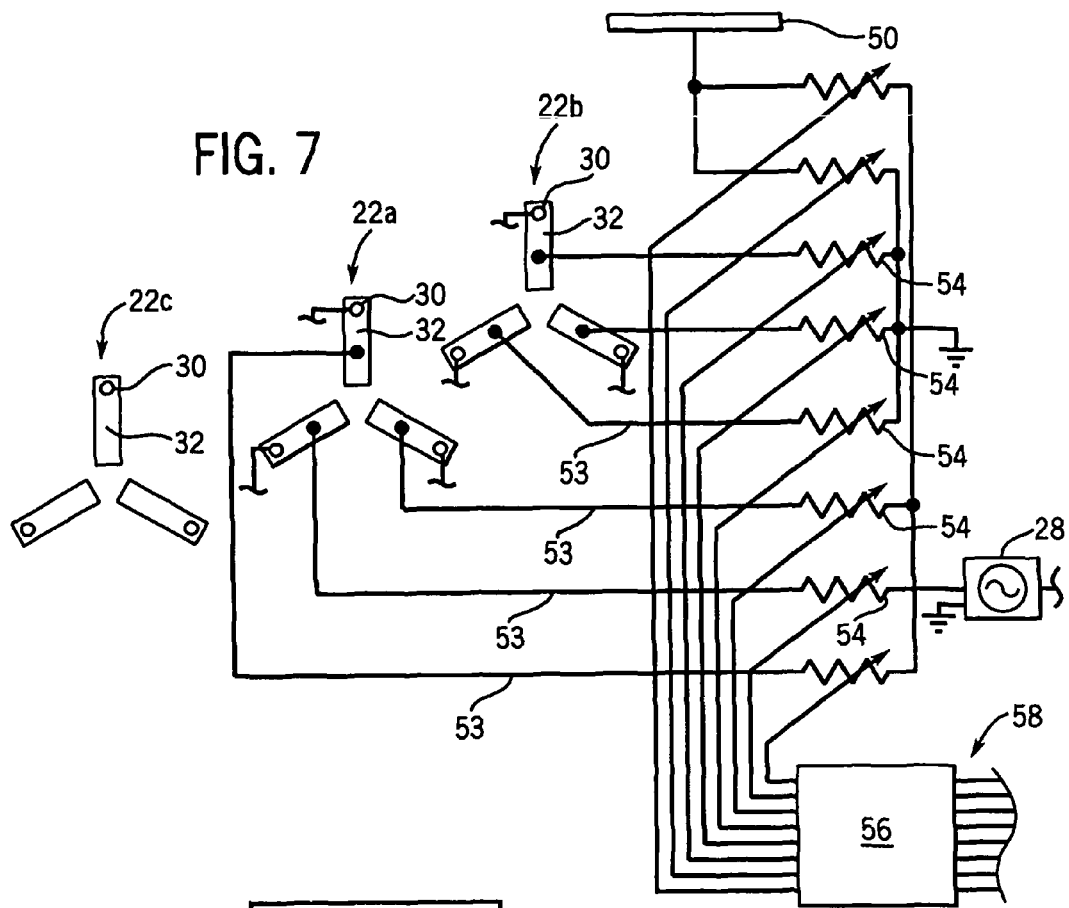
FIG. 7 is a figure similar to that of FIGS. 2 and 5 showing yet another embodiment in which wires of each of the first and second electrodes are electrically isolated so that independent voltages or currents or phases of either can be applied to each wire to precisely tailor the current flow between that wire and the other electrodes.

Referring now to FIG. 7, these principles may be applied to a system in which each wire 32 of electrodes 22a and 22b is electrically isolated within the electrode assemblies 16a and 16b and driven by separate feeds by switch 53 through variable resistances 54 connected either to the power oscillator 28 or its return. Electrically isolated means, in this context, that there is not a conductive path between the electrodes 22a and 22b except through tissue prior to connection to the power supply or control electronics. As noted before, a phase difference can also be employed between separate feeds from switch 53 to further control the path of current flow between electrode wires 32. This phase difference could be created, e.g. by complex resistances that create a phase shift or by specialized waveform generators operating according to a computer program, to produce an arbitrary switching pattern. The values of the resistances 54 are changed as will be described by a program operating on a controller 56. For this purpose, the variable resistances 54 may be implemented using solid-state devices such as MOSFETs according to techniques known in the art.

Likewise, similar variable resistances 54 also controlled by a controller 56 may drive the contact plate 50.

For the purpose of control, the controller 56 may receive the inputs from the temperature sensors 30 (described above) of each wire 32 as lines 58. This separate control of the voltages on the wires 32 allows additional control of current flows throughout the tumor 12 to be responsive to heat sinking blood vessels or the like near any one wire.

Figure 8:
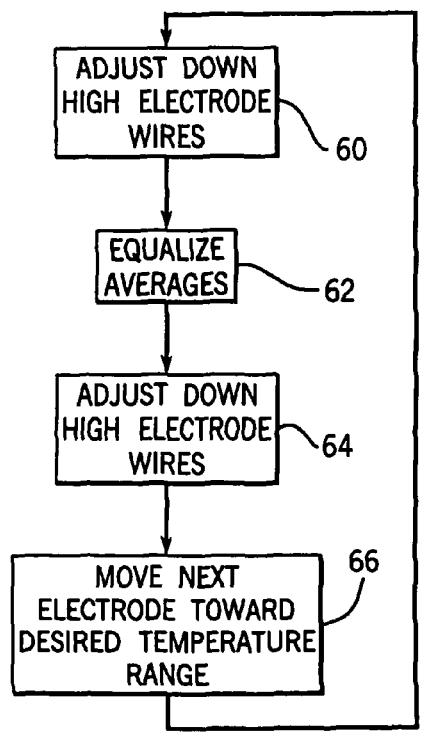
FIG. 8 is a flow chart of a program as may be executed by the controller of FIG. 7 in utilizing its multi-electrode control.

Referring to FIG. 8, one possible control algorithm scans the temperature sensors 30 as shown by process block 60. For each temperature sensor 30, if the temperature at that wire 32 is above a "ceiling value" below a tissue charring point, then the voltage at that wire is reduced. This "hammering down" process is repeated until all temperatures of all wires are below the ceiling value.

Next at process block 62, the average temperature of the wires on each electrode 22a and 22b is determined and the voltage of the contact plate 50 is adjusted to incrementally equalize these average values. The voltage of the contact plate 50 is moved toward the voltage of the electrode 22 having the higher average.

Next at process block 64, the hammering down process of process block 60 is repeated to ensure that no wire has risen above its ceiling value.

Next at process block 66 one wire in sequence at each occurrence of process block 66 is examined and if its temperature is below a "floor value" below the ceiling value, but sufficiently high to provide the desired power to the tumor, the voltage at that wire 32 is moved incrementally away from the voltage of the wires of the other electrode 22. Conversely, if the wire 32 is above the floor value, no action is taken.

Incrementally, each wire 32 will have its temperature adjusted to be within the floor and ceiling range by separate voltage control. It will be understood that this process can be applied not only to the control parameter of temperature but also to other desired control parameters including, for example, impedance.

As shown in FIG. 7, this process may be extended to an arbitrary number of electrodes 22 including a third electrode set 22c whose connections are not shown for clarity.

While this present invention has been described with respect to umbrella probes, it will be understood that most of its principles can be exploited using standard needle probes. Further, it will be understood that the present invention is not limited to two electrode sets, but may be used with multiple electrode sets where current flow is predominantly between sets of the electrodes. The number of wires of the umbrella electrodes is likewise not limited to three and commercially available probes suitable for use with the present invention include a 10 wire version. Further, although the maximum temperatures of the electrodes were used for control in the above-described examples, it will be understood that the invention is equally amenable to control strategies that use minimum or average temperature or that measure impedance or use predetermined switching times.

II. Multiplexed Monopolar Electrode Operation

Referring now to FIGS. 9a and 9b, a multiplexed monopolar system 70 provides a power oscillator 28 having a power output 72 at which a radio-frequency signal is connected to the pole of a single pole double throw switch 74. Switch 74 is preferably implemented as a solid-state switch according to techniques well known in the art preferably, but not limited to, switching at speeds over 20 kilohertz.

A first throw 76 of the switch 74 is connected to a first electrode 22a being an umbrella-type electrode as described above with the tines of the umbrella electrically joined. At least one tine may include a temperature sensor 30a.

A second throw 78 of the switch 74 is connected to second electrode 22b also having a temperature sensor 30b.

The electrodes 22a and 22b are placed as described above flanking the volume of a tumor or in separate tumors as may be desired. If a single tumor is being treated, the electrodes 22a and 22b will be proximate to each other typically less than three times the diameter of the extension radius of the tines of the electrodes 22a and 22b. Conversely, to the bipolar embodiment, in the multiplexed monopolar electrode operation, there is no limitation on the orientation at which the probes are inserted. It is also understood that the described technique can be extended to any number of electrodes 22.

In one embodiment, signals from the temperature sensors 30a and 30b are received by a controller 56, which subtracts the temperatures to create a temperature difference signal that is received by a proportional/integral (PI) type controller 56. PI controllers are well known in the art and produce an output signal that is a function of a first control constant $K_1$ times the input difference signal, plus a second control constant $K_2$ times the integral of the input difference signal. The PI controller 56 in this case produces a control signal 80 implemented as an electrical square wave whose further properties will be described below.

As an alternative to the temperature difference signal, the PI controller may accept a variety of other control inputs including impedance, temperature, power, absolute time (for a regular switching among electrodes), or the difference between the impedance, temperature, or power of one or more electrodes and other similar control inputs.

Alternatively to the PI controller, any other conceivable control mechanism can be implemented to distribute the power to two or more probes.

Referring also to FIG. 10, generally, the square wave of the control signal 80 controls the operation of the pole of the switch 74 to create a switching pattern 82a for electrode 22a and a switching pattern 82b for electrode 22b. The switching patterns 82a and 82b describe the position of the pole of the switch 74 and thus a modulation envelope of the radio-frequency waveform of the output 72 seen at each electrode 22a and 22b. During times when the pole of the switch 74 is connected to throw 76, the wave form 82a is in a high state indicating that radio-frequency power is being supplied to electrode 22a. Conversely, when the pole of the switch 74 is connected to throw 78, wave form 82b is high indicating that radio-frequency energy is being supplied to electrode 22b.

As is illustrated in the preferred embodiment, signals 82a and 82b are exact complements indicating that only one of electrodes 22a and 22b will be receiving electrical power at any given instant and yet the power from the power oscillator 28 is fully utilized. That is, when electrode 22a is energized, current flows only between electrode 22a and contact plate 50 (as indicated by arrow 84a of FIGS. 9a and 9b). Conversely, when electrode 22b is energized, current flows only between electrode 22b and contact plate 50 (as indicated by 84b of FIGS. 9a and 9b). When only one of electrodes 22a and 22b is activated at a given time, there is no shielding that would tend to distort lesion volume 90a about electrode 22b or 90b about electrode 22b and that would otherwise occur if electrodes 22a and 22b were simultaneously energized. Note, however, that some overlap of the "on" states of electrodes 22a and 22b may be tolerated if it is minor in comparison to the period of non-overlap.

A period of time 94a during which electrode 22a is activated expressed as a ratio with a period of time 94 during which electrode 22b is activated, defines a "duty-cycle". The control signal 80 forming the output of the PI controller 56 controls this duty-cycle so that power is steered preferentially to one of electrodes 22a and 22b having the lower temperature. In this way, the controller 56 may act to bring their relative temperatures of the two electrodes 22a and 22b into equilibrium. Alternatively, the duty-cycle may be controlled based on impedance between the connected pairs of electrodes or power dissipated between the connected pairs of the electrodes. The speed at which the duty-cycle is adjusted in response to temperature differences and controlled by the settings of $K_1$ and $K_2$ described above and is adjusted to reflect average temperatures at the electrodes 22a and 22b whose actual temperatures may deviate instantaneously with the switching of power.

The frequency of the switching of switch 74 is selected to be fast compared to the cooling time of the tissue (e.g., 2 Hz or above). Higher switching speeds above 10 kHz and near 20 kHz may be preferred to avoid low-frequency components that could excite nerves and tissue, especially cardiac tissue. Switching is performed preferentially at the zero-crossings of the signal provided by the radio-frequency power supply to avoid transient currents.

The PI controller may also provide a limiter reducing the average power delivered to electrodes 22a and 22b when a threshold temperature (approximately 95 degrees C.) is reached by decreasing simultaneously periods 94a and 94b while preserving their ratio. In this case, the patterns 82a and 82b are no longer complementary but still have non-overlapping high states.

The power output of the radio-frequency power supply may further be controlled by the temperature or impedance of electrodes 22a and 22b. In this embodiment, patterns 82a and 82b are complementary. The switch is controlled in a way to bring temperatures of electrodes 22a and 22b to equilibrium. The power output of the radio-frequency power supply is adjusted to bring average temperature of electrodes 22a and 22b to a set temperature, typically below the temperature where charring and boiling would occur.

In an alternative embodiment shown in FIG. 9b, the temperature sensors 30a and 30b may be routed as indicated by dotted lines 96 to a secondary switch 98 being a single pole, double throw switch whose pole is connected to a temperature input on a standard power oscillator 28. In this case, the power oscillator 28 may be directly controlled so as to reduce its output voltage or current as a function of the temperature received from a given temperature probe 30a or 30b such as will alternate according to the operation of the switch 74. Thus during the time the power oscillator 28 is delivering power to electrode 22a, it will also be receiving the temperature from temperature sensor 30a to control it appropriately. Then when switch 74 changes state and the power oscillator is connected to electrode 22b, the power oscillator may receive a temperature signal from temperature 30b.

Referring now to FIG. 11, the switch 74 may in fact accommodate any number of electrodes 22a, 22b, and 22c here depicted as needle electrodes in multiple tumors 12 and 12'. Thus the present invention may provide the benefits of locating an arbitrary number of electrodes in place about a tumor at one instant and then providing essentially simultaneous treatment of the volume with combined thermal effects without the need to move electrodes.

As depicted, switch 74 is a single pole, triple throw switch with one throw connected to each of electrodes 22a, 22b and 22c to provide modulated radio-frequency energy according to patterns 82c, 82d, and 82e as shown in FIG. 12. Switching patterns 82c, 82d, and 82e are analogous to switching patterns 82a and 82b described above except for the fact that the duty-cycle of three wave forms 82a, 82b and 82c is independently controlled (per arrows 83) to proportionally move power to the lowest temperature electrode 22, and they are no longer complementary but simply have non-overlapping on times. Ideally, when one or more electrodes 22 have temperatures below the threshold, one of the switching patterns 82c, 82d, and 82e is on at all times. In certain control algorithms there may be cycles, where power is not steered to any of the probes. In that case on pole of the multi throw switch is not connected to any probe, or is connected to some element dissipating the power.

It is specifically intended that the present invention not be limited to the embodiments and illustrations contained herein, but include modified forms of those embodiments including portions of the embodiments and combinations of elements of different embodiments as come within the scope of the following claims. For example, the switch may be implemented using multiple radio-frequency sources that are enabled and disabled appropriately. Hybrid systems in which multiple electrodes are energized simultaneously and alternating are also contemplated. While percutaneous electrodes are described, the invention is also applicable to cauterizing probes and operative or laparoscopically placed electrodes.

We claim:

1. A method of non-microwave ablation of a tumor having a volume, the method reducing electrical shielding caused by simultaneous activation of electrodes and comprising the steps of:
   (a) separately placing at least two physically independent electrodes at edges of the tumor;
   (b) connecting a source of radiofrequency power having a frequency to a first electrode to provide resistive heating of tissue at the first electrode;
   (c) after a first time, disconnecting the source of radiofrequency power from the first electrode to define a first duty cycle at the first electrode;
   (d) after step (c) connecting the source of radiofrequency power to a second electrode to provide resistive heating of tissue at the second electrode;
   (e) after a second time, disconnecting the source of radiofrequency power from the second electrode to define a second duty cycle at the second electrode;
   (f) repeating steps (b) through (e) while varying the first and second duty cycles to deliver different levels of power to the first and second electrodes dependent on a sensed condition of the tissue while also energizing the first and second electrodes at different, substantially non-overlapping times independent of the sensed condition.

2. The method of claim 1 wherein each of a first and second on-times of the first and second duty cycles are substantially longer than a period of the frequency of the radiofrequency power.

3. The method of claim 1 further including the steps of sensing a temperature at the first and second electrodes and further controlling the first and second duty cycles according to the sensed temperatures to maximize power delivery to the tumor within the constraint of energizing the first and second electrodes at substantially non overlapping times.

4. The method of claim 1 further including the steps of sensing the impedance at the first and second electrodes and further controlling the first and second duty cycles according to the sensed impedances to maximize power delivery to the tumor within the constraint of energizing the first and second electrodes at substantially non overlapping times.

5. The method of claim 1 further including a third electrode providing a common power return for the source of radiofrequency power.

6. The method of claim 1 wherein the first and second electrodes are inserted through the skin to a site of the tumor.

7. The method of claim 1 wherein the first and second electrode, when disconnected from the source of radiofrequency power, are isolated from the source of radiofrequency power.

8. An apparatus for ablating a tumor having a volume comprising:
- at least two electrodes positionable at edges of the tumor;
- a source of non-microwave radiofrequency power having a frequency;
- a switch system operating to:
  - (a) connect the source of radiofrequency power to a first electrode to provide resistive heating of tissue at the first electrode;
  - (b) after a first time, disconnecting the source of radiofrequency power from the first electrode to define a first duty cycle at the first electrode;
  - (c) after step (b) connecting the source of radiofrequency power to a second electrode to provide resistive heating of tissue at the second electrode;
  - (d) after a second time, disconnecting the source of radiofrequency power from the second electrode to define a third duty cycle at the third electrode;
  - (e) repeat steps (b) through (d) while varying the first and second duty cycles to deliver different levels of power the first and second electrodes dependent on a sensed condition of the tissue while also energizing the first and second electrodes at different, substantially non-overlapping times independent of the sensed condition.

9. The apparatus of claim 8 wherein each of a first and second on-times of the first and second duty cycles are substantially longer than a period of the frequency of the radiofrequency power.

10. The apparatus of claim 8 further including a temperature sensor sensing temperature at the first and second electrodes and wherein the switch system further controls the first and second, duty cycles based on the sensed temperatures to maximize power delivery to the tumor.

11. The apparatus of claim 8 further including an impendence sensor sensing the impedance at the first and second electrodes and wherein the switch system controls the first and second duty cycles based on the sensed impedances to maximize power delivery to the tumor.

12. The apparatus of claim 8 further including a third electrode providing a common power return for the source of radiofrequency power.

13. The apparatus of claim 8 wherein the first and second electrodes are adapted to be inserted through the skin to a site of the tumor.

14. The apparatus of claim 8 wherein the switch system disconnects each first and second electrode from the source of radiofrequency power without grounding the electrode.

* * * * *